(12) United States Patent
Link et al.

(10) Patent No.: US 12,303,391 B2
(45) Date of Patent: May 20, 2025

(54) HIP JOINT IMPLANT WITH RESHAPEABLE FASTENING BRACKETS

(71) Applicant: WALDEMAR LINK GmbH & Co. KG, Hamburg (DE)

(72) Inventors: Helmut D. Link, Hamburg (DE); Hans-Joachim Fischer, Norderstedt (DE)

(73) Assignee: WALDEMAR LINK GmbH & Co. KG, Hamburg (DE)

( * ) Notice: Subject to any disclaimer, the term of this patent is extended or adjusted under 35 U.S.C. 154(b) by 617 days.

(21) Appl. No.: 17/613,995

(22) PCT Filed: May 20, 2020

(86) PCT No.: PCT/EP2020/064109
§ 371 (c)(1),
(2) Date: Nov. 24, 2021

(87) PCT Pub. No.: WO2020/239585
PCT Pub. Date: Dec. 3, 2020

(65) Prior Publication Data
US 2022/0226121 A1    Jul. 21, 2022

(30) Foreign Application Priority Data
May 24, 2019   (EP) .................................... 19176517

(51) Int. Cl.
*A61F 2/34*   (2006.01)
*A61F 2/30*   (2006.01)
*A61F 2/32*   (2006.01)

(52) U.S. Cl.
CPC ............ *A61F 2/30749* (2013.01); *A61F 2/34* (2013.01); *A61F 2002/30014* (2013.01);
(Continued)

(58) Field of Classification Search
CPC ........................................................ A61F 2/34
See application file for complete search history.

(56) References Cited

U.S. PATENT DOCUMENTS 5,425,778 A   6/1995  Zichner et al.
5,702,477 A   12/1997  Capello et al.
(Continued)

FOREIGN PATENT DOCUMENTS

DE        41 02 510 A1      7/1992
DE        19901710 A1  *    7/2000  ............... A61F 2/34
(Continued)

OTHER PUBLICATIONS

English Translation of DE 41 02 510 A1 (Year: 1992).*
(Continued)

*Primary Examiner* — Brian A Dukert
(74) *Attorney, Agent, or Firm* — Chiesa Shahinian & Giantomasi PC

(57) ABSTRACT

Hip joint implant for fastening to a pelvic bone (9), with a support body which has a socket (6) and whose convex outer face is designed to bear on the pelvic bone (9) and which, on its concave inner face, has a receiving seat for a pelvis-side bearing that is designed to receive a joint head of a femoral component of a hip prosthesis, and with outwardly directed flat fastening brackets (2, 3) which are arranged at the edge region of the socket (6) and are each provided with at least one receiving seat for a fastening means. The fastening brackets (2, 3) are made of a reshapeable biocompatible material and are connected to the socket (6) via a non-releasable cohesive bond (7), wherein the socket (6) is made of another, stiffer biocompatible material. A high degree of robustness of the socket (6) is thus combined with what is, by virtue of the reshapeability, an improved adaptation to the anatomical conditions of the respective pelvic bone. This (Continued)

improves reliability of fastening, stability and long-term behavior.

20 Claims, 3 Drawing Sheets

(52) U.S. Cl.
CPC ............... *A61F 2002/30578* (2013.01); *A61F 2002/3241* (2013.01); *A61F 2002/3401* (2013.01); *A61F 2310/00023* (2013.01)

(56) References Cited

U.S. PATENT DOCUMENTS

| | | | |
|---|---|---|---|
| 5,755,806 | A | 5/1998 | Stalcup et al. |
| 2009/0088865 | A1 | 4/2009 | Brehm |
| 2013/0297036 | A1* | 11/2013 | Collins .................... A61F 2/34 623/22.24 |
| 2021/0077262 | A1 | 3/2021 | Lee et al. |
| 2022/0226121 | A1 | 7/2022 | Link et al. |

FOREIGN PATENT DOCUMENTS

| | | |
|---|---|---|
| FR | 2784289 A1 | 4/2000 |
| FR | 2785522 A | 5/2000 |
| FR | 2 837 092 A1 | 9/2003 |
| JP | H07434 A | 1/1995 |

OTHER PUBLICATIONS

Translation for Imhof DE 199 01 710 A1 (Year: 2000).*
International Search Report and Written Opinion mailed Aug. 13, 2020 in corresponding International Application No. PCT/EP2020/064109 and the English Translation of the International Search Report.
Search Report dated Aug. 13, 2019 issued in corresponding European Application No. 19176517.1.
Extended European Search Report mailed Mar. 14, 2024 in connection with European Patent Application No. 23206857.7, filed Oct. 30, 2023, 6 pgs.
Extended European Search Report mailed Nov. 21, 2024 in connection with European Patent Application No. 24198102.6, 18 pgs. (including translation).

* cited by examiner

HIP JOINT IMPLANT WITH RESHAPEABLE FASTENING BRACKETS

CROSS-REFERENCE TO RELATED APPLICATIONS

This application is the National Stage entry under 35 U.S.C. § 371 of International Application No. PCT/EP2020/064109 filed on May 20, 2020, published on Dec. 3, 2020 under Publication Number WO 2020/239585 A1, which claims the benefit of priority under 35 U.S.C. § 119 of European Patent Application Number 19176517.1 filed May 24, 2019, the entireties of which are herein incorporated by reference.

The invention relates to a hip joint implant for fastening to a pelvic bone, with a support body which has a socket and whose convex outer face is designed to bear on the pelvic bone and which, on its concave inner face, has a receiving seat for pelvis-side bearing components that are designed to receive a joint head of a femoral component of a hip prosthesis, and with outwardly directed flat fastening brackets which are arranged at the edge region of the socket and are each provided with at least one receiving seat for a fastening means. It further relates to a method for producing such hip joint implants.

Hip joints may suffer degeneration through disease or through wear. Hip joint endoprostheses have proven useful for therapy. These comprise a femoral component, which is implanted at the upper end of the thigh bone, and a hip component, which interacts with the femoral component and is implanted in the pelvic bone (acetabulum). In many cases, it can happen that the pelvic bone is damaged in the region of the hip joint. This has the effect of making it difficult to fasten the hip joint component to the pelvic bone. This is especially true of implants that function as a partial replacement of the pelvis. These have additional fastening elements in order not only to achieve secure anchoring of the joint socket of the hip joint implant on the pelvic bone, but also to stabilize the pelvic bone itself.

Hip joint implants of this kind are known, for example, from U.S. Pat. No. 5,702,477. They have a plurality of fastening elements on a support body that comprises the actual joint socket. These fastening elements comprise elongate brackets which extend in a cranial direction and which are provided with a plurality of drilled holes to permit fastening by means of a bone screw. Moreover, opposite these fastening brackets, a caudally directed and shorter bracket is provided, which can optionally also be configured like a hook. They serve to securely fasten and stabilize the implant, and in particular the joint socket thereof, on a damaged pelvic bone.

Hip joint implants with such fastening brackets are also produced and sold by the applicant as a partial replacement of the pelvis. For reasons of cost-effective production and a high degree of mechanical robustness, the material chosen is stainless steel (implant steel). This affords the advantage that, on the one hand, the support body with the socket is sufficiently robust and has sufficient mechanical stability, and, on the other hand, the fastening brackets can be easily adapted by reshaping during surgery, depending on the individual anatomy of the patient and the bone defect that is to be bridged. Although a solution is thus achieved that is satisfactory in functional terms, there is still the difficulty that, for reasons of better biocompatibility, titanium is often the preferred material. A tried and tested material for implants is TiAl6V4 which, although sufficiently robust, nevertheless has the disadvantage that it cannot be reshaped during surgery. Pure titanium, by contrast, is much easier to reshape, but, due to a lack of dimensional stability, it is not routinely used for the pelvic socket component. This conflict of objectives has not hitherto been able to be satisfactorily resolved.

The object of the invention is to create an improved hip joint implant that avoids these disadvantages. The invention moreover extends to a corresponding production method.

The solution according to the invention lies in the features of the independent claims. Advantageous developments are the subject matter of the dependent claims.

In a hip joint implant for fastening to a pelvic bone, with a support body which has a socket and whose convex outer face is designed to bear on the pelvic bone and which, on its concave inner face, has a receiving seat for a pelvis-side bearing component that is designed to receive a joint head of a femoral component of a hip prosthesis, and with outwardly directed flat fastening brackets which are arranged at the edge region of the socket and are each provided with at least one receiving seat for a fastening means, provision is made according to the invention that the fastening brackets are made of a reshapeable (cold-formable) biocompatible material and are connected to the socket via a non-releasable cohesive bond, wherein the socket is made of another, stiffer biocompatible material.

Firstly, some of the terms used are explained below:

"Reshapeable" is understood to mean a material that is plastically deformable at room temperature, such that fastening brackets formed from this material can be manually adapted, with or without hand tools, to an underlying structure. This is also referred to as cold-formable.

In contrast to this, non-cold-formable material denotes material that cannot be plastically deformed manually or using hand tools at room temperature.

Biocompatible is understood to mean a material that is approved and suitable for the production of implants and endoprostheses.

The bearing component can be designed as an insert which is made of a material that promotes sliding and which functions as a receiving seat and sliding partner for a joint head. Such an insert is usually fastened by being cemented or clamped in the support body, but other types of fastening can also be provided. The bearing component can also be designed, however, as an interposition component. This is usually understood to mean an intermediate piece of this type that changes an opening angle of the socket, in particular for adaptation to particular anatomical conditions. The element forming the sliding partner for the joint head is then received in this intermediate piece. Moreover, the bearing component can also be introduced into and fixed in the support body as a dual mobility insert.

The invention is based on the concept of a division of material, in the sense that different materials are used for the fastening brackets and the socket-like support body, and these materials are cohesively and therefore permanently connected to one another. The fastening brackets are produced from a reshapeable, biocompatible material, for example pure titanium (grade 2, grade 3 or grade 4). This material can also be easily reshaped intraoperatively by the surgeon, so that the latter can easily achieve a good adaptation to the respective individual peculiarities of the pelvic bone of the respective patient. By contrast, for the support body with the socket, which by means of a bearing component forms the bearing for the joint head of the femoral component, another biocompatible material is used, for example a standard titanium alloy such as TiAl6V4. This material is stiffer, cost-effective, mechanically robust and only marginally reshapeable. However, the latter is not even necessary for the socket at all; on the contrary, the lack of reshapeability increases the robustness and dimensional accuracy of the socket, even under high loads. By virtue of the dimensional accuracy, the construction according to the invention is particularly suitable for sockets of modular design, with alternative sockets and socket inserts being used if necessary.

The invention has recognized that the hitherto unresolved conflict between a robust and cost-effective implant, on the one hand, and good reshapeability for better adaptation and fastening to the individual shape of the pelvic bone, on the other hand, can be resolved in this way. By virtue of the cohesive bond between the fastening brackets and the socket, it achieves this without compromising on the fastening safety, stability and long-term strength of the hip joint implant. The associated disadvantages of a multi-part, screwed construction, as is known from DE 41 02 510 A1, are thereby effectively avoided. In addition, the cohesive bond not only increases reliability, it also reduces the installation space compared to the known screw connection.

The cohesive bond is expediently designed as a welded connection, in particular as an electron beam welded connection. This affords the advantage of a high degree of reproducibility and an excellent welding result with minimal heat input. As a result of the low heat input, there is also only an extremely small amount of distortion. Furthermore, it permits the welding of various materials, in particular of (pure) titanium with titanium alloys. Finally, this connection permits a high degree of automation, which likewise benefits the reproducibility and therefore the quality of the connection as a whole.

The cohesive bond is advantageously designed with a welded-through weld seam. A square butt weld, which permits reliable fastening and safe through-welding with little heat input, is particularly expedient.

The fastening brackets can in principle be configured individually. However, in the context of the present invention, it is particularly preferable to design the fastening brackets in one piece with a fastening ring, which engages around the socket-like support body and is connected to the socket by means of the cohesive bond. This provides for good pre-assembly, namely of the fastening brackets to the fastening ring. After this has been prefabricated (and, if necessary, reworked), it can be pre-assembled with the socket-like support body. The pre-assembly permits logical provisioning before the components are welded. In order to ensure a high degree of positioning accuracy, the pre-assembly preferably comprises pressing the socket-like support body onto the fastening ring and the fastening brackets arranged thereon.

The fastening brackets can be prefabricated with openings for fastening means. In most cases, these will be drilled holes that are prepared in order to receive fastening screws (bone screws) for fastening the bracket to the pelvic bone. Furthermore, the fastening ring can be prefabricated to the extent that it has an opening which is dimensioned in such a way that it functions to receive the socket-like support body. The opening is preferably prefabricated exactly with respect to an external dimension of the support body, in particular to an external diameter of the socket of the support body. It is particularly advantageous to design the opening in the fastening ring in such a way that it forms an interference fit with the socket-like support body. This permits an initial fixing, which favors pre-assembly.

The socket itself can be made of a non-cold-formable material, for example a titanium alloy that is less deformable than pure titanium. For example, an alloy of TiAl6V4 that achieves a tensile strength of 800 MPa or greater has proven useful for this purpose, with pure titanium only achieving a tensile strength of ca. 300 MPa. For the fastening brackets or the fastening ring, pure titanium has proven useful, in particular pure titanium according to grade 2, grade 3 or grade 4. It combines a high degree of biocompatibility with good reshapeability.

The socket is preferably provided with a support shoulder and/or a centering ring in the region where the fastening ring is received. The support shoulder is expediently designed circumferentially. It can thus form a stop for the fastening ring, such that the position of the latter is defined when the fastening ring is pushed onto the socket. The centering ring ensures an exactly central position. It can also serve as an interface for a modular system. This makes it possible to use other types of sockets too, for example sockets that belong to a modular system consisting of several components. These can also include sockets that are designed differently but have a uniform external diameter. This is especially true when several uniform external diameters are provided, which are graduated in different external diameter sizes.

The transition region between the socket and fastening brackets or fastening ring can be provided with a milled surface. This can be applied, for example, as part of secondary processing after the cohesive bonding. On the one hand, this makes the fastening ring smaller and, on the other hand, the surface quality is improved.

The fastening brackets can be preformed. This affords the advantage that a rough adaptation to the typical anatomical structure of the pelvic bone can already be achieved. For fine adjustment, the surgeon simply needs to bend the brackets accordingly. This results in considerably less work.

The invention further relates to a method for producing a corresponding hip joint implant.

For a detailed explanation, reference is made to the above description.

The invention is explained in more detail below on the basis of an illustrative embodiment and with reference to the accompanying drawing, in which.

Figure 1:
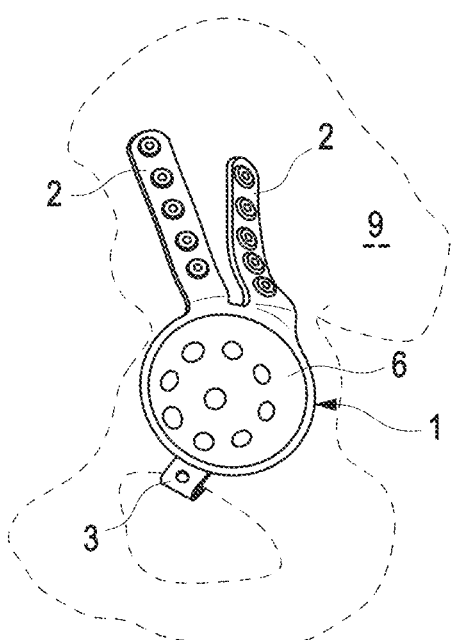
FIG. 1 shows an illustrative embodiment of the hip joint implant in the state when fitted on a pelvic bone.

An illustrative embodiment of a hip joint implant according to the invention is shown in FIG. 1 in a state when fitted on a pelvic bone 9 (acetabulum).

The hip joint implant is designated as a whole by reference number 1 and comprises a socket-like support body 6 on which two flat and elongate fastening brackets 2 are arranged pointing upward (cranially). A shorter fastening bracket 3, extending downward (caudally), is provided on the opposite side of the socket-like support body 6 (in the following also called socket for short).

In the illustrative embodiment shown, the implant 1 is composed of two components, namely the socket 6 and a fastening component, which comprises the fastening brackets 2, 3 and a fastening ring 4, on which the fastening brackets 2, 3 are arranged. The fastening brackets 2 are each elongate, flat elements which are provided with a multiplicity of bores 21 for receiving fastening means. The fastening bracket 3 is likewise a flat element, but, in the illustrative embodiment shown, it is shorter and wider than the fastening brackets 2. This embodiment is only an example; the invention is not limited thereto. The fastening bracket 3 is likewise provided with a plurality of bores 31 for receiving fastening means. The bores 21, 31 are designed as through-openings for receiving a fastening means (not shown). Screws known per se, in particular bone screws, function as fastening means.

Figure 2:
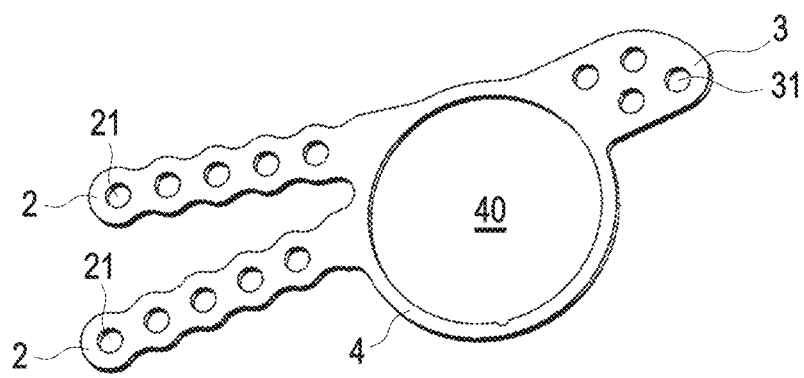
FIG. 2 shows a view of a prefabricated fastening ring with fastening brackets.

Reference is now made to FIG. 2. The fastening brackets 2, 3 are arranged protruding radially outward on a ring 4, which is designated as a fastening ring. In the illustrative embodiment shown, the fastening brackets 2, 3 and the fastening ring 4 are made in one piece. They are made of a titanium material, namely pure titanium of grade 2 or grade 4. This material has extremely good biocompatibility and moreover has the advantage that it can also be easily deformed manually. It is therefore possible for the operator to reshape the fastening brackets 2, 3 even during the implantation, i.e. during the operation, if necessary, and thus better adapt them to the particular anatomical features of the pelvic bone 9 of the respective patient. The one-piece design of the fastening ring 4 ensures a high degree of strength and good handling.

The fastening ring 4 delimits an inner region 40 which is designed to receive the socket-like support body 6. In the illustrative embodiment shown, the fastening ring 4 is designed fully circumferentially, although this is not absolutely necessary; the ring does not need to be completely closed.

Figure 3:
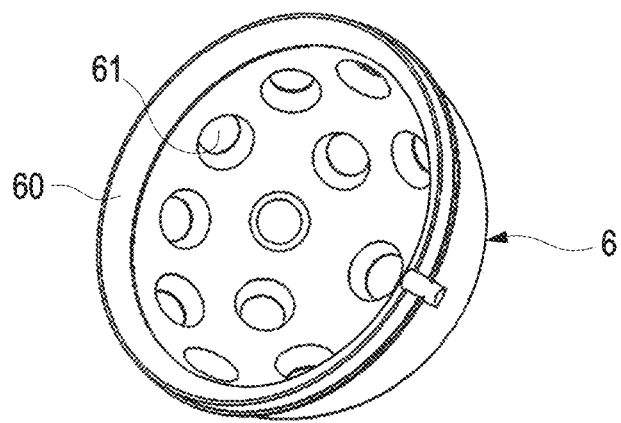
FIG. 3 shows a perspective view of a socket-like support body.

The socket-like support body 6 shown in FIG. 3 has a substantially hemispherical shape. Its main part is curved in a dome shape and provided with a multiplicity of fastening bores 61. On its convex outer face, the socket-like support body 6 is designed to bear against the bone surfaces of the pelvic bone 9 and for this purpose is expediently provided with a surface or coating that promotes the incorporation of bone substance. On its inner face, the socket-like support body is correspondingly concave and, together with a bearing component, forms the receiving seat for a joint head (not shown) of a femoral component of a hip joint prosthesis. As bearing component, a bearing shell 8 (see FIGS. 6 and 7) made of material that promotes sliding can be inserted in the socket 6. In a variant, the bearing shell 8 can optionally also be designed for dual mobility. In this case, the bearing shell basically consists of two bearing shells nested one inside the other, namely an outer shell 81 and an inner shell 82. A further bearing surface 83 is thus obtained between them (shown in FIG. 6 by a dashed line). The additional degree of freedom achieved reduces wear and tear between the bearing shell 8 and the socket 6; moreover, greater mobility can thus be achieved, and therefore improved protection against dislocation.

The socket-like support body 6 is made of a biocompatible titanium alloy, which has quite a high degree of strength in order to take up the bearing forces of the hip joint. TiAl6V4 in particular has proven useful as a titanium alloy. It has a high degree of strength and robustness. It is typically too stiff to be bent by hand. It is therefore particularly suitable for taking up the considerable bearing forces of the hip joint, which are exerted by the joint head, and leading them into the pelvic bone 9.

Figure 4:
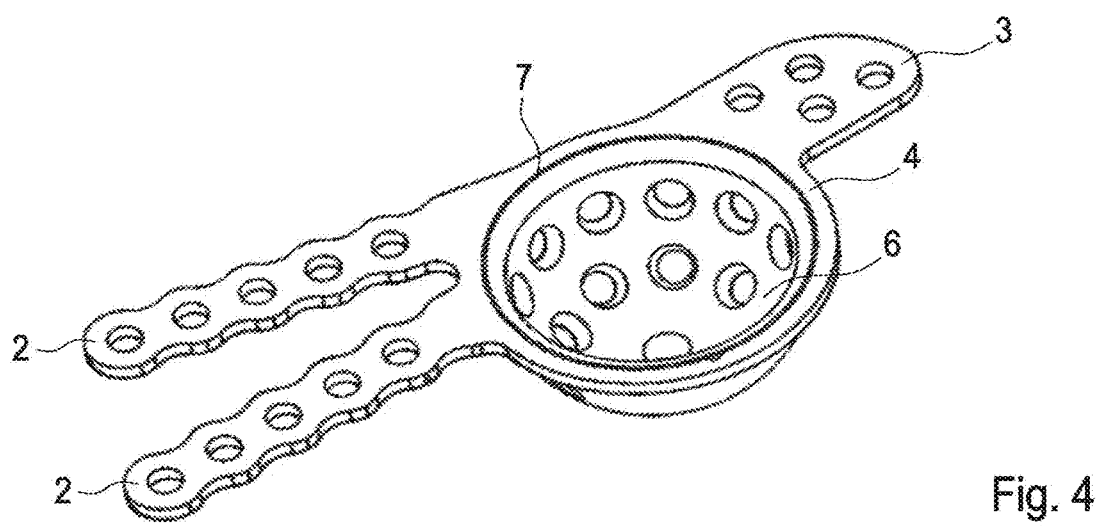
FIG. 4 shows a perspective view of a pre-assembled state.
Figure 5:
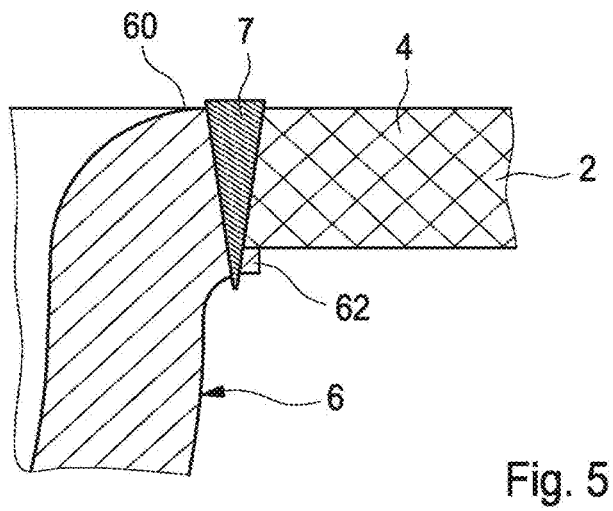
FIG. 5 shows a cross-sectional view of a weld seam as a connection between fastening ring/brackets and support body.

During production, the socket-like support body 6 is pre-assembled by being inserted into the opening 40 of the fastening ring 4. It is inserted until the fastening ring 4, in the region of the upper end on the socket edge 60, engages with an exact fit around the socket-like support body 6, preferably with an interference fit. Thus, in a pre-assembled state, the socket-like support body 6 is retained on the fastening ring 4 with fastening brackets 2, 3, as is shown in FIG. 4. In this state, a cohesive bond 7 between the socket 6 and the fastening ring 4 with the fastening brackets 2, 3 can then be produced by electron beam welding. The cohesive bond 7 is preferably designed with a welded-through weld seam, in particular what is called a square butt weld, as is shown in FIG. 5. The welded connection 7 ensures a firm connection even between different materials, namely in the present case between the titanium alloy TiAl6V4 for the socket 6 and pure titanium (grade 2 or grade 4) for the fastening brackets 2, 3 with their fastening ring 4.

Figure 6:
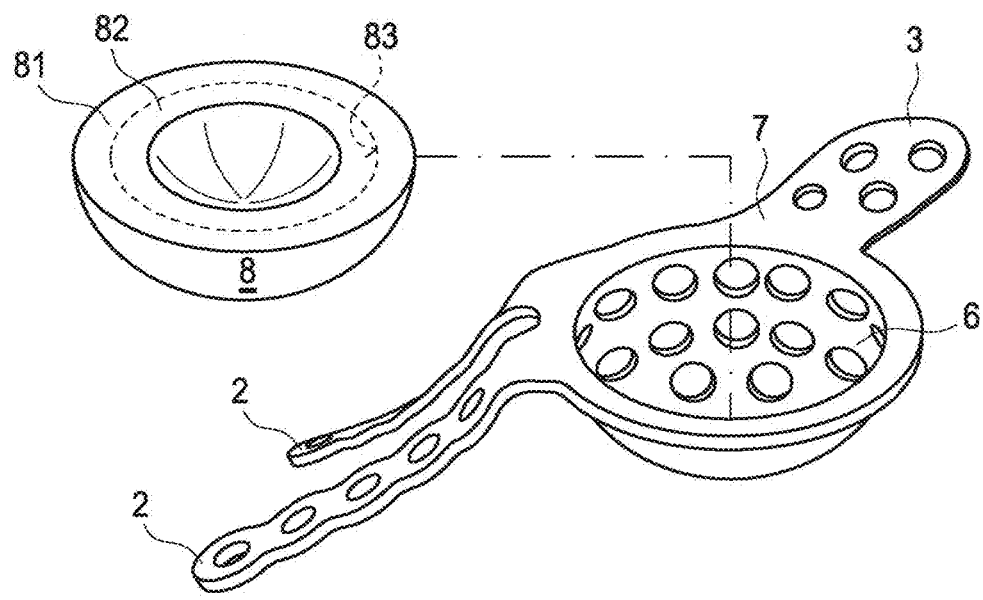
FIG. 6 shows a perspective view of a completed hip joint implant, with bent fastening brackets and with a bearing component that is ready for assembly.
Figure 7:
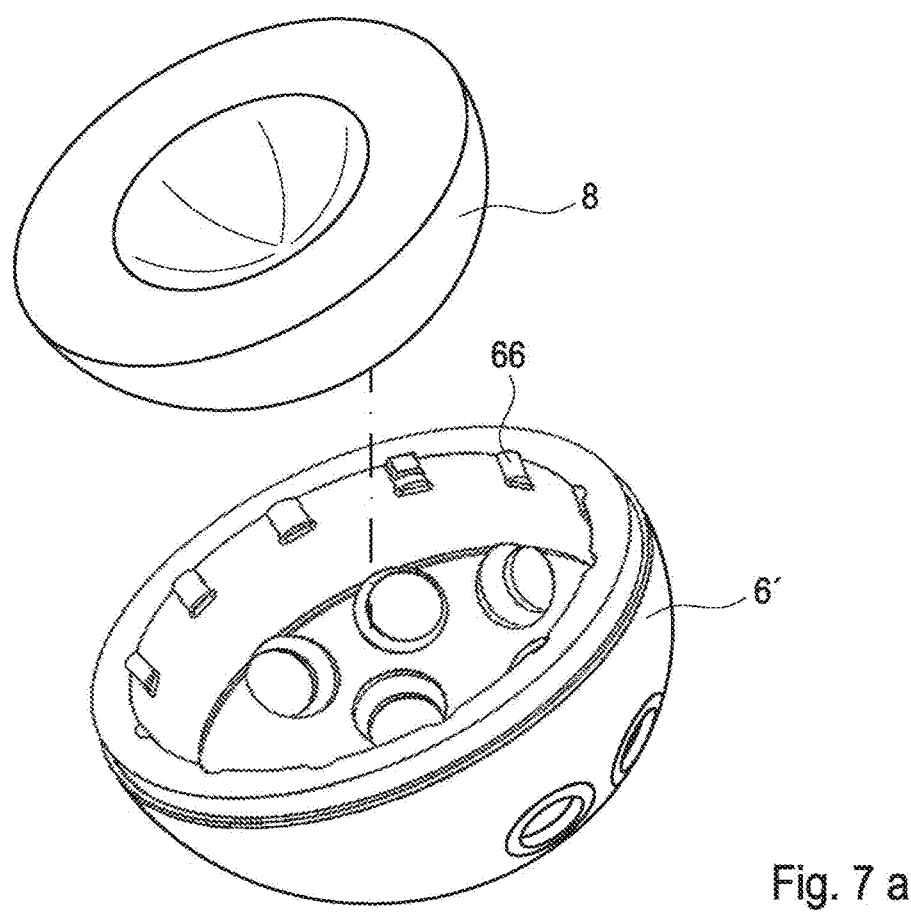
FIGS. 7a, b show an embodiment of the socket-like support body in a modular construction.
Figure 7:
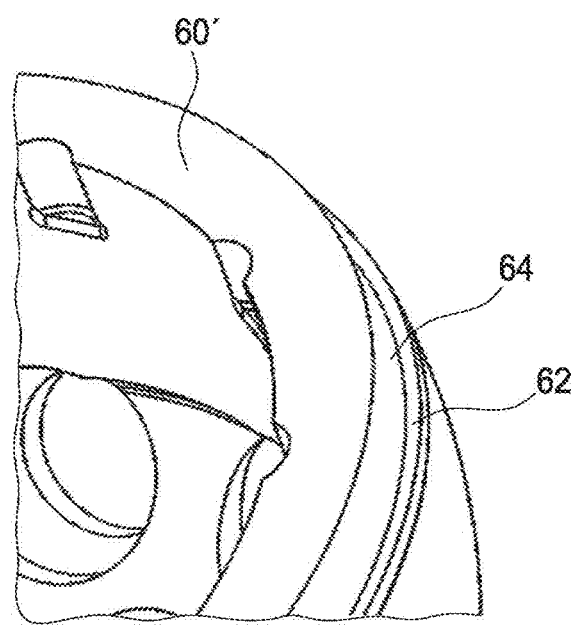

FIG. 5 also reveals a support shoulder 62 which ensures that the fastening ring 4, with the fastening brackets 2, 3 arranged thereon, is positioned and supported on the socket 6. In particular, a flat and level arrangement is obtained such that a surface that is as continuous as possible is formed at the top. Provision can preferably also be made that, after the production of a welded connection 7, it is possible, by overmilling, to create a smooth transition of the top between the socket 6, with its socket edge 60, the welded connection 7 and the top of the fastening ring 4. This final state is shown in FIG. 6.

Finally, the fastening brackets can already be at least partially pre-formed. This is also shown in FIG. 6. Here, the fastening brackets 2 are already pre-formed to a contour of the pelvic bone 9, as is typically to be expected. Fine adaptation to the respective individual anatomy of the pelvic bone can then be carried out intraoperatively by the surgeon, simply by bending the fastening brackets 2, 3 by hand.

The invention can be used in the context of a modular hip joint system. Here, differently configured sockets 6, 6' are provided, which differ in particular in terms of their size (dimensioning). Thus, sockets 6 of different sizes can be provided, although they are connectable in the same way, by means of the welded connection 7, to the fastening ring 4 with the fastening brackets 2, 3. However, the modular sockets can also differ in terms of their further configuration, in particular in terms of the configuration of the inner face. A modularly configured socket 6' of this kind is shown in FIG. 7a. It has positioning grooves 66 for precision-angle positioning of modular bearing inserts (not shown). A bearing shell 8 can be inserted into the socket 6, as has already been explained above for FIG. 6.

Optionally, a centering ring 64, as shown in FIG. 7b, can be formed on the socket 6. In terms of its external diameter, it is precisely matched to the width of the opening 40 and thus permits precise fitting and centering of the socket 6 in relation to the fastening ring 4 with the fastening brackets 2, 3. Particularly when using a modular socket 6', a centering ring 64 can be used to achieve secure positioning and centering even of sockets of different sizes. The centering ring 64 can be designed as a separate element or, particularly in the case of sockets having relatively large dimensions, can also be designed as a recess and thus be made in one piece with the socket 6.

The invention claimed is:

1. A hip joint implant for fastening to a pelvic bone comprising:
   a support body comprising a socket with a convex outer face designed to bear on the pelvic bone; a concave inner face with a receiving seat to receive a joint head of a femoral component of a hip prosthesis, wherein the support body comprises a top between the convex outer face and the concave inner face; and a fastening ring comprising at least two outwardly directed flat fastening brackets arranged at the edge of the fastening ring and providing at least one opening for receiving the support body, wherein the fastening ring is dimensioned to extend around a perimeter of the support body, and wherein the top of the support body and a top of the fastening ring form a flat, level surface.

2. The hip implant joint of claim 1, wherein the fastening brackets are made of a reshapeable biocompatible material.

3. The hip implant joint of claim 1, wherein the fastening brackets are connected to the socket via a non-releasable cohesive bond, and the socket is made from a more stiff biocompatible material.

4. The hip joint implant of claim 3, wherein the cohesive bond is a welded connection.

5. The hip joint implant of claim 4, wherein the welded connection is an electron beam welded connection.

6. The hip joint implant of claim 5, wherein the cohesive bond has a welded-through weld seam.

7. The hip joint implant of claim 1, said fastening ring engaging around the support body and connected to the support body by a cohesive bond.

8. The hip joint implant of claim 7, wherein the fastening brackets are prefabricated with openings for fastening, and the fastening ring is prefabricated with an opening for receiving the support body.

9. The hip joint implant of claim 1, wherein an external diameter of the support body is dimensioned to enable an interference fit between the support body and the fastening ring.

10. The hip joint implant of claim 1, wherein the support body is made of a non-cold-formable material.

11. The hip joint implant of claim 1, wherein the support body is made of a titanium alloy which is less formable than pure titanium with tensile strength of at least 800 MPa.

12. The hip joint implant of claim 1, wherein the fastening brackets are made of pure titanium of grade 2, 3, or 4, and the support body is made of a titanium alloy.

13. The hip joint implant of claim 1, wherein the support body has a circumferential support shoulder, wherein the circumferential support shoulder is configured to contact a bottom of the fastening ring, wherein the bottom of the fastening ring is opposite the top of the fastening ring.

14. The hip joint implant of claim 1, wherein the support body has a transition region between the support body and fastening brackets comprising a milled surface.

15. A modular hip joint system comprising: the hip joint implant of claim 1, further comprising a plurality of sockets which are differently configured but have a uniform external diameter.

16. The modular hip joint system of claim 15, wherein a plurality of uniform external diameters are provided graduated in different sizes.

17. A method for producing a hip joint implant for fastening to a pelvic bone, with a support body which has a socket and whose convex outer face is designed to bear on the pelvic bone and which, on a concave inner face, together with a bearing component, forms the seat for receiving a joint head of a femoral component of a hip prosthesis, wherein the support body comprises a top between the convex outer face and the concave inner face, and with a fastening ring comprising outwardly directed flat fastening brackets which are arranged at the edge region of the fastening ring and are each provided with at least one opening for receiving the support body, the method comprising:

prefabricating the support body and the socket from a first material, prefabricating the fastening brackets from a reshapeable, biocompatible second material, pre-assembly of the fastening brackets on the support body, welding of the fastening brackets to the support body, and milling support body and the socket so that a top of the support body and the top of the fastening ring form a flat, level surface.

18. The method of claim 17, wherein the welding is electron beam welding.

19. The method of claim 17, wherein the welding step is an electron beam welding, forming a welded-through weld seam.

20. The method of claim 17, wherein the support body has a circumferential support shoulder, wherein the circumferential support shoulder is configured to contact a bottom of the fastening ring, wherein the bottom of the fastening ring is opposite the top of the fastening ring.

\* \* \* \* \*